(12) United States Patent
Sasso

(10) Patent No.: US 6,562,046 B2
(45) Date of Patent: *May 13, 2003

(54) SCREW DELIVERY SYSTEM AND METHOD

(75) Inventor: Rick Sasso, Indianapolis, IN (US)

(73) Assignee: SDGI Holdings, Inc., Wilmington, DE (US)

(*) Notice: Subject to any disclaimer, the term of this patent is extended or adjusted under 35 U.S.C. 154(b) by 49 days.

This patent is subject to a terminal disclaimer.

(21) Appl. No.: 09/876,397

(22) Filed: Jun. 7, 2001

(65) Prior Publication Data

US 2001/0027320 A1 Oct. 4, 2001

Related U.S. Application Data

(63) Continuation of application No. 09/448,361, filed on Nov. 23, 1999.

(51) Int. Cl.[7] ............................................. A61B 17/56
(52) U.S. Cl. .............................. 606/96; 606/80; 606/98
(58) Field of Search ............................. 606/80, 96, 97, 606/98, 104

(56) References Cited

U.S. PATENT DOCUMENTS

| | | |
|---|---|---|
| 3,719,186 A | 3/1973 | Merig, Jr. |
| 3,892,232 A | 7/1975 | Neufeld |
| 3,964,480 A | 6/1976 | Froning |
| 4,292,964 A | 10/1981 | Ulrich |
| 4,549,538 A | 10/1985 | Schadrack, III et al. |
| 4,573,448 A | 3/1986 | Kambin |
| 4,667,664 A | 5/1987 | Taylor et al. |
| 4,714,076 A | 12/1987 | Comte et al. |
| 4,872,451 A | 10/1989 | Moore et al. .................. 128/92 |
| 5,013,317 A | 5/1991 | Cole et al. |
| 5,049,150 A | 9/1991 | Cozad |
| 5,139,500 A | 8/1992 | Schwartz |
| 5,154,720 A | 10/1992 | Trott et al. |
| 5,178,621 A | 1/1993 | Cook et al. |
| 5,201,729 A | 4/1993 | Hertzmann et al. |
| 5,364,399 A | 11/1994 | Lowery et al. ................ 606/69 |
| 5,392,766 A | 2/1995 | Masterson et al. |
| 5,395,317 A | 3/1995 | Kambin |
| 5,439,464 A | 8/1995 | Shapiro |
| 5,458,604 A | 10/1995 | Schmieding |

(List continued on next page.)

FOREIGN PATENT DOCUMENTS

| | | |
|---|---|---|
| WO | WO 95/35180 | 12/1995 |
| WO | WO 99/52446 | 10/1999 |

OTHER PUBLICATIONS

Bernard, Jeanneret, MD. Arthrodesis with Facet Screws, *Lumbosacral and Spinopelvic Fixation*. 1996; 51:655–666.

Jacobs et al. Enhancement of Lumbar Spine Fusion by Use of Translaminar Facet Joint Screws, *Spine*. 1989; vol. 14, No. 1:12–15.

Grob, D. et al. Translaminar screw fixation in the lumbar spine: technique, indications, results, *Eur–Spine J.* 1998; 7:178–186.

(List continued on next page.)

*Primary Examiner*—Ralph A. Lewis
(74) *Attorney, Agent, or Firm*—Woodward, Emhardt, Naughton, Moriarty & McNett LLP

(57) ABSTRACT

A screw delivery system and method are disclosed for use in a variety of surgical indications. The screw delivery system generally comprises an outer cannula, a guide, and various interventional devices such as bone drill bits and taps as well as an implant driver for inserting a screw. The method disclosed varies by indication, but is ordinarily intended for use as a minimally invasive procedure which is a combination of percutaneous and open techniques wherein a small midline incision is made over a surgical site and the screw delivery system provides a percutaneous portal through an incision distant from the small midline incision over the surgical site.

32 Claims, 6 Drawing Sheets

U.S. PATENT DOCUMENTS

| | | | |
|---|---|---|---|
| 5,484,437 | A | 1/1996 | Michelson |
| 5,531,751 | A | 7/1996 | Schultheiss et al. |
| D374,283 | S | 10/1996 | Michelson .................. D24/135 |
| 5,601,550 | A | 2/1997 | Esser |
| 5,643,274 | A | 7/1997 | Sander et al. |
| 5,658,293 | A | 8/1997 | Vanlaningham |
| 5,667,509 | A | 9/1997 | Westin |
| 5,667,513 | A | 9/1997 | Torrie et al. |
| 5,669,915 | A | 9/1997 | Caspar et al. |
| 5,730,744 | A | 3/1998 | Justin et al. |
| 5,741,266 | A | 4/1998 | Moran et al. |
| 5,746,743 | A | 5/1998 | Greenberg |
| 5,810,828 | A | 9/1998 | Lightman et al. |
| 5,836,950 | A | 11/1998 | Hansson |
| 5,895,389 | A | 4/1999 | Schenk et al. |
| 5,895,390 | A | 4/1999 | Moran et al. |
| 5,899,908 | A | 5/1999 | Kuslich et al. |
| 5,899,998 | A | 5/1999 | McGauley et al. ......... 707/104 |
| 5,904,685 | A | 5/1999 | Walawalker |
| 5,947,970 | A | 9/1999 | Schmelzeisen |
| 6,004,326 | A | 12/1999 | Castro et al. .................. 606/99 |
| 6,027,506 | A | 2/2000 | Faccioli et al. |
| 6,221,082 | B1 | 4/2001 | Marino et al. .............. 606/130 |
| 6,224,603 | B1 | 5/2001 | Marino ......................... 606/79 |
| 6,287,313 | B1 * | 9/2001 | Sasso ........................... 606/96 |

OTHER PUBLICATIONS

Benini et al. Selective decompression and translaminar articular facet screw fixation for lumbar canal stenosis and disc protrusion, *British Journal of Neurosurgery*. 1993; 7:413–418.

*Primary Posterior fusion C1/2 in Odontoid Fractures: Indications, Technique, and Results of Transarticular Screw Fixation*, Jeanneret and Magerl, *Journal of Spinal Disorders*, vol. 3, No. 4, pp. 464–475, 1992.

*Stable Posterior Fusion of the Atlas and Axis by Transarticular Screw Fixation*, Magerl, Seemann, St. Gallen, *Cervical Spine I*, 1987.

*In Vitro Investigations of Internal Fixation Systems of the Upper Cervical Spine*, Wilke, Fischer, Kugler, Magerl, Claes, Worsdorfer, *European Spine Journal*, 1992.

*Atlanto–Axial Fusio with Transarticular Screw Fixation, The Journal of Bone and Joint Surgery*, British Volume, vol. 73–B, Nov. 1991, pp. 972–976.

*Osteology—The Skeleton, Gray's Anatomy*, pp. 33–54, 1977.

"Triad™: Tri–Columnar spinal EndoArthrodesis™ via Minimally Invasive Guidance," NuVasive Publication (1page). (no date).

"NuVasive: Safe, Reproducible Percutaneous Access To The Spine," brochure (6 pages). (no date).

NuVasive™: Creative Spine Technology™—Company Profile ©2000 by NuVasive, Inc. (2 pages).

"Cannulated Screws for Odontoid Screw Fixation and Atlantoaxial Transarticular Screw Fixation," by Curtis A. Dickman, M.D. et al., *J. Neurosurg.* Dec. 1995, vol. 83, pp. 1098–1100.

"UCSS™: Universal Cannulated Screw Set" Medtronic Sofamor Danek brochure (4 pages). (Feb. 1997).

Technical Bulletin #1—Oct. 28, 1996. "Universal Cannulated Screw Set" by Brad Winn (5 pages).

"Screw Insertion Cannula Set," AcroMed Spine Tools brochure, ©1996 AcroMed Corporation (4 pages).

Cortical Lag Screw Drawing and Information (1 page) (no date).

Medtronic Sofamor Danek Instruments Drawings and Descriptions (1 page) ©2000.

\* cited by examiner

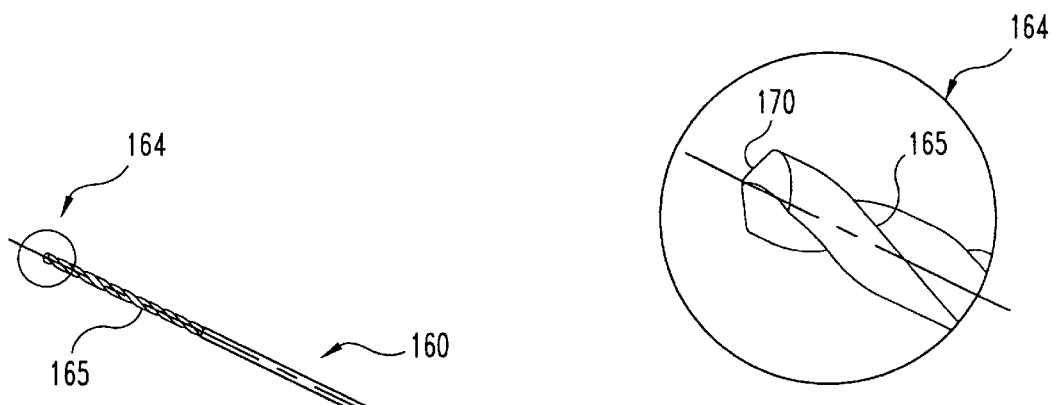
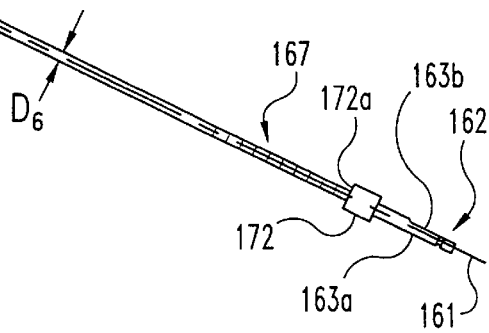
Fig. 4A
Fig. 4B
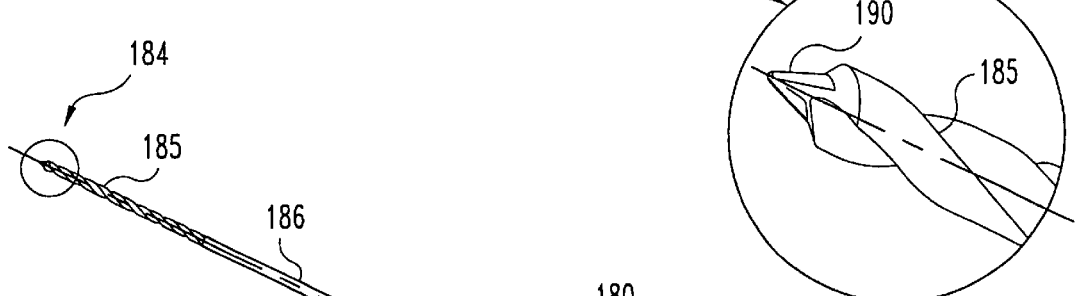
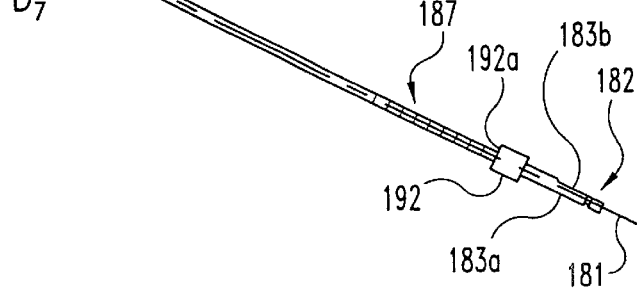
Fig. 5A
Fig. 5B

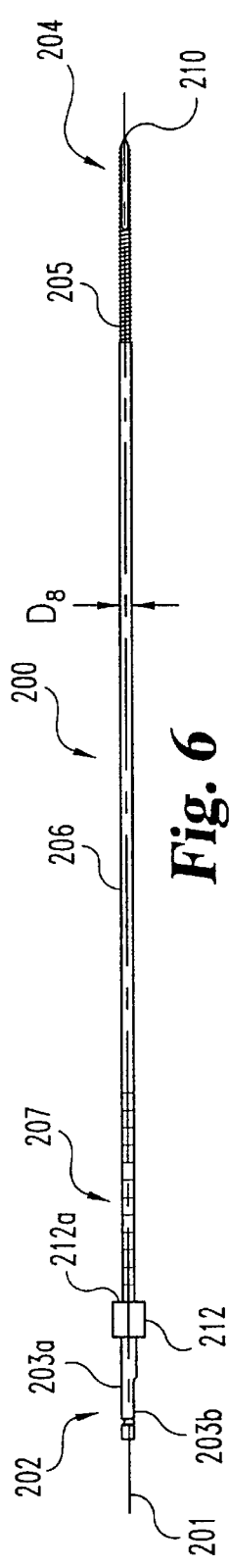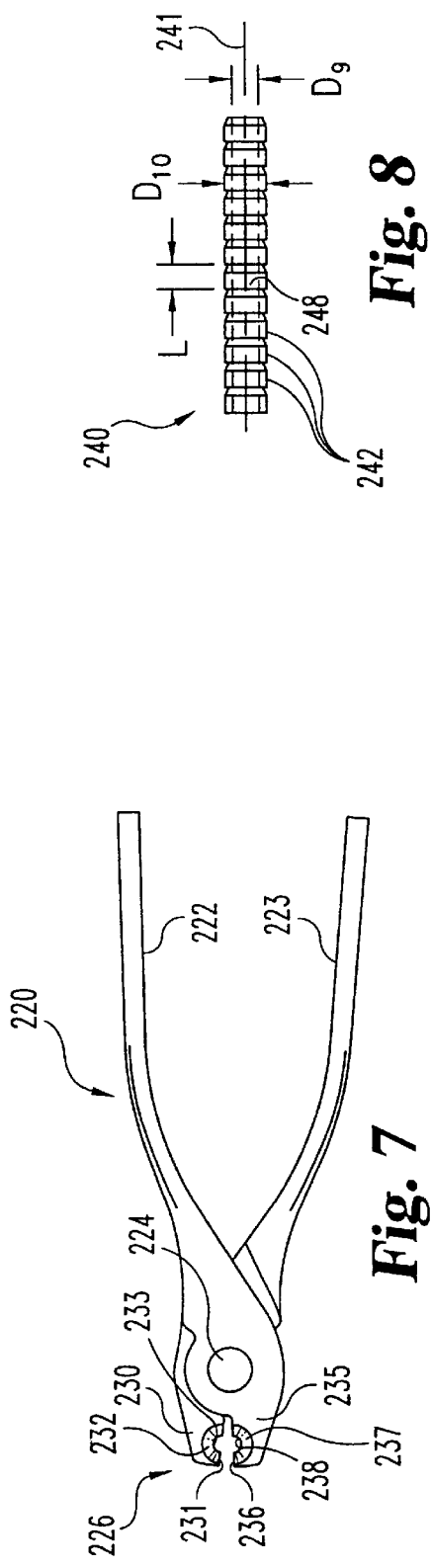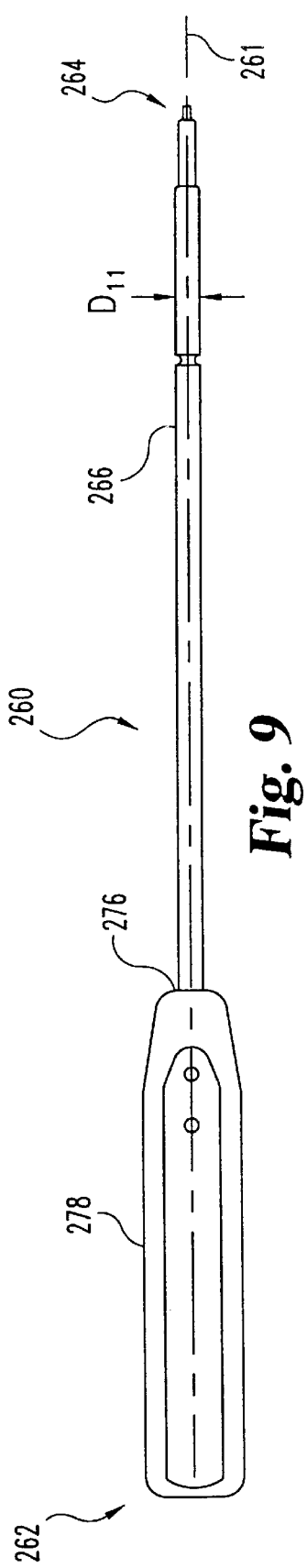

SCREW DELIVERY SYSTEM AND METHOD

This is a continuation of application Ser. No. 09/448,361, filed Nov. 23, 1999.

BACKGROUND

The human spine is a flexible weight bearing column formed from a plurality of bones called vertebrae. There are 33 vertebrae which are named based on which of five regions (cervical, dorsal, lumbar, sacral, and coccygeal) in which they are found. Going from the top of the spine down, in general there are seven cervical vertebra, twelve dorsal vertebra, five lumbar vertebra, five sacral vertebra, and four coccygeal vertebra. The vertebra of the cervical, dorsal, and lumbar regions of the spine are separate throughout the life of an individual, but the vertebra of the sacral and coccygeal regions in an adult are fused to form two bones, the five sacral vertebra entering into the formation of the sacrum and the four coccygeal vertebra into the coccyx. In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. Also, the second cervical vertebra (axis vertebra) has an odontoid process, which is a strong, prominent process, shaped like a tooth, rising perpendicularly from the upper surface of the body of the axis vertebra. Further details regarding the construction of the spine are known to those of ordinary skill in the art and may be found in such common references as *Gray's Anatomy*, Crown Publishers, Inc., 1977, pp. 33–54, which is herein incorporated by reference.

The past two decades have seen greatly increased use of implants for the stabilization of fractures and/or fusion of various portions of the spine. These implant devices include a variety of longitudinal elements such as rods or plates which span two or more vertebra and are affixed to the vertebra by various fixation elements such as wires, staples, and screws (often inserted through the pedicles of the vertebra). These systems may be affixed to either the posterior or the anterior side of the spine. In many cases, these implant systems are prominent beneath the skin and have a higher profile than more simple fixation devices. One such simpler fixation device is in the stable posterior fusion of the atlas and axis vertebra by transarticular screw fixation using the technique of Magerl et al. disclosed in *Stable Posterior Fusion of the Atlas and Axis by Transarticular Screw Fixation*, F. Magerl, P-S. Seeman, *Cervical Spine*, Volume 1, Springer-Verlag, Copyright 1987, pp. 322–327; *Primary Posterior Fusion 1-2 in Odontoid Factors; Indications, Technique, and Results of Transarticular Screw Fixation*, B. Jeanneret and F. Magerl, *Journal of Spinal Disorders*, Volume 5, No. 4, pp. 464–475, 1992, Raven Press, Ltd., New York; (also see *Atlanto-Axial Fusion With Transarticular Screw Fixation*, D. Grob, B. Jeanneret, M. Aebi, and T. M. Markwalder, *The Journal of Bone and Joint Surgery*, Volume 73-B, No. 6, 1991, pp. 972–976) all of which are herein incorporated by reference.

The use of transarticular screw fixation in both fusion procedures and stabilization procedures for fractures has undergone increasing use. However, due to the small entry angle of the screw with respect to the back of a patient lying prone on the operating table, procedures making use of transarticular screw fixation have required extremely long and wide midline incisions in order to place the screws as necessary in various procedures in both the cervical and lumbar spine regions. These large incisions result in increased operating time with consequent increase in blood loss as well as enlarging the size of the scar left on the patient. It should be understood that while reduction of pain and maintaining range of motion are the surgical goal, the size of the incision and the scar it leaves behind are often the only visible measure a patient will have to judge the quality of the surgeon's work. Thus, it is preferable if the incision is made in a manner not only to preserve the skin's contour, but of a minimum length and size to increase patient satisfaction.

SUMMARY OF THE INVENTION

One embodiment of the present invention is a screw delivery system kit for providing a minimally invasive portal with a small entry angle to a surgical site, comprising an outer cannula, a trocar, a guide and a bone drill bit. The outer cannula has a first exterior surface and a first interior surface defining a bore. The first interior surface has a first inner diameter and the first exterior surface has a first outer diameter. The surfaces extend along a first length on a first axis between a first proximal end having a first stop and a first distal end. The trocar has a second exterior surface with a second outer diameter. The second exterior surface extends along a second length on a second axis between a second proximal end having a second stop defined thereon and a second distal end defining a blunt tip. The guide has a handle and a tube. The tube has a third exterior surface and a third interior surface defining a passageway. The third interior surface has a third inner diameter and the third exterior surface has a third outer diameter. The third interior surface extends between a third proximal end and a third distal end. The third exterior surface extends along a third length on a third axis between a third stop at the third proximal end and the third distal end. The handle is connected to the tube at an angle to the third axis. The bone drill bit has a fourth exterior surface with a fourth outer diameter extending along a fourth length on a fourth axis between a fourth stop located near a fourth proximal end and a plurality of drilling flutes defined on a fourth distal end.

Another embodiment of the invention is a method of inserting a screw through a minimally invasive portal comprising making a first incision for viewing over a surgical site and making a second incision spaced apart from the first incision. Then an outer cannula having a bore defined between a proximal end and a distal end and a trocar through the bore are inserted into the second incision. The outer cannula and trocar are advanced toward the surgical site until the distal end contacts the surgical site at which time the trocar is withdrawn from the outer cannula. An opening in the bone is then drilled followed by screwing a screw into the opening in the bone.

Yet another embodiment of the present invention is a screw delivery system kit for providing a minimally invasive portal to a surgical site comprising: an outer cannula; a trocar; means for drilling an opening in a bone at the surgical site; means for aiming said means for drilling; and means for screwing a screw into the opening in the bone.

BRIEF DESCRIPTION OF THE DRAWINGS

FIG. 4A is a standard bone drill bit for use in a screw delivery system of the present invention.

FIG. 4B is an enlarged portion of the bone drill bit tip of FIG. 4A.

FIG. 5A is a side view of an improved bone drill bit for use with the screw delivery system of the present invention.

FIG. 5B is an enlarged view of the tip of the bone drill bit of FIG. 5A.

FIG. 6 is a side view of a bone tap for use with the present invention.

FIG. 7 is a side view of a cutter for adjusting the length of the adjustable length stop of FIG. 8.

FIG. 8 is a side view of an embodiment of an adjustable length stop of the present invention.

FIG. 9 is a side view of a screwdriver for use in the screw delivery system of the present invention.

DESCRIPTION OF THE PREFERRED EMBODIMENTS

Figure 1:
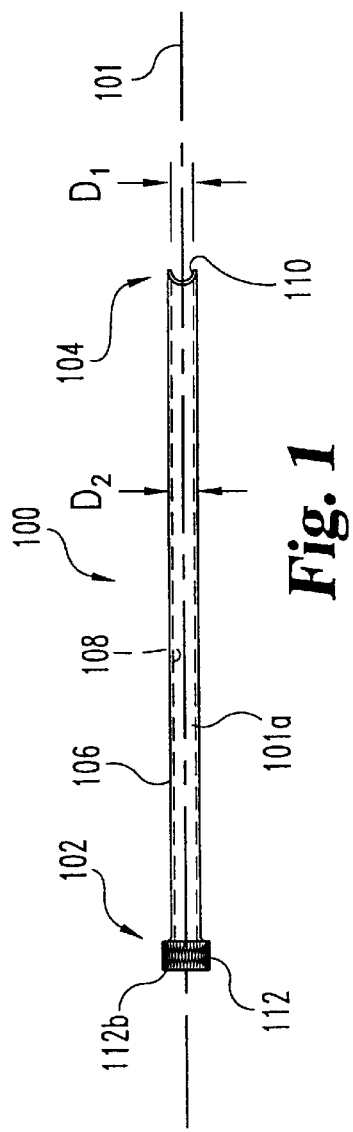
FIG. 1 is a side view of the outer most cannula of a screw delivery system of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

With respect to FIG. 1 there is illustrated outer cannula 100 extending along longitudinal axis 101. Outer cannula 100 provides the primary passageway for screw implantation to a surgical site through a percutaneous portal (as discussed further below) distant from the surgical site. Many of the spinal surgeries for which the screw delivery system and method of the present invention will find use in involve very small entrance angles for the screw with respect to the spine of a patient lying prone. The outer cannula 100 has a bore 101a extending between the near end 102 and far end 104 of the outer cannula 100. Outer cannula 100 has an exterior surface 106 and an interior surface 108, interior surface 108 defining bore 101a. The far end 104 of outer cannula 100 terminates in a tip 110. Tip 110 is shown as having serrations with a crescent moon-like shape for ease of contacting the surgical site (i.e., bone of a vertebra). It should be understood, however, that the tip 110 may take a variety of shapes and forms other than the crescent moon illustrated.

The near end 102 of outer cannula 100 has an annular flange or stop 112. Bore 101a also extends through the annular flange 112. The stop 112 acts in combination with the stops on other devices inserted through the bore 101a of the outer cannula to prevent over-insertion of the various bone drill bits, taps, and other probes and interventional devices and prevents possible damage to the surgical site resulting from over-insertion. It should be understood that stop 112 need not be in the shape of an annular flange, but may simply be a plurality of projections extending from the exterior surface 108 of outer cannula 100. It should be further understood that the stop 112 of outer cannula 100 may also be simply the circumference of the exterior surface 108 of outer cannula 100 at the near end 102. This is because the stops of the other probes or interventional devices (e.g., bone drill bits, bone taps, guides) will contact the circumference of the near end 102 of the exterior surface 106 of outer cannula 100. It should also be understood that the preferred embodiment is for outer cannula 100 to possess an annular flange 112. Outer cannula 100 has an inner diameter D1 for bore 101a and an outer diameter D2 as illustrated in FIG. 1.

Figure 2:
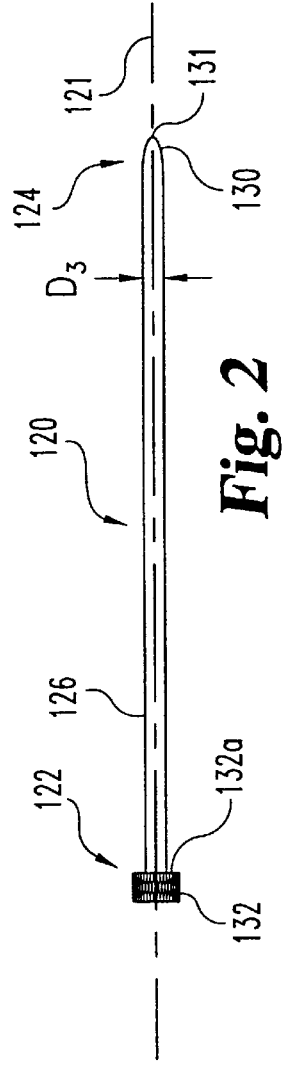
FIG. 2 is a trocar for use with the outer cannula of FIG. 1 for initial insertion of the screw delivery system into the patient.
Figure 11:
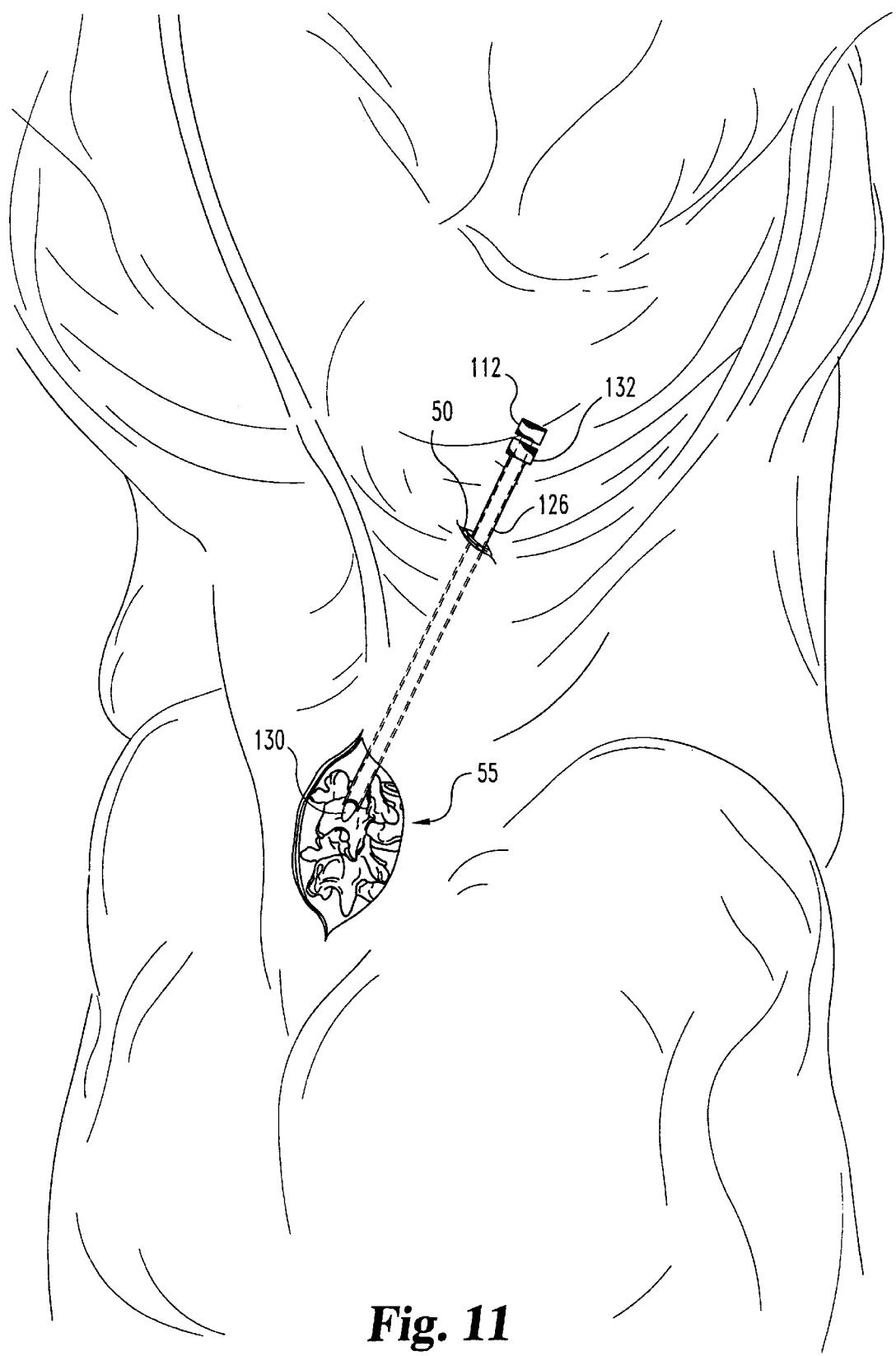
FIG. 11 is an illustration of the insertion of the bullet-shaped trocar of FIG. 2 through the outer cannula of FIG. 1 creating a percutaneous portal in the back distal from a lumbar vertebra surgical site.

With respect to FIG. 2 there is illustrated a trocar 120 extending along a longitudinal axis 121 between a proximal end 122 and a distal end 124. Trocar 120 is preferably, but not necessarily, a solid shaft having an exterior surface 126 between the proximal end 122 and the distal end 124. The distal end 124 of trocar 120 has a bullet-shaped head 130 with a blunt tip 131 for minimizing the trauma to the tissue as the combination of the trocar 120 and the outer cannula 100 are used as a soft tissue penetrator or introducer from a distal incision 50 on the back to the surgical site 55 of the vertebra (see FIG. 11). Trocar 120 has an annular flange or stop 132 at the proximal end 122. The exterior surface 126 of trocar 120 has an outer diameter D3. The outer diameter D3 of trocar 120 is less than the inner diameter D1 of outer cannula 100 which is in turn less than the outer diameter D2 of outer cannula 100. Since the outer diameter D3 is less than the inner diameter D1, the exterior surface 126 of trocar 120 may be inserted through the bore 101a of outer cannula 100. It should be understood that to act as a soft tissue penetrator, the trocar 120 need merely have an unbroken surface at bullet-shaped head 130 and whatever other portion extends beyond the far end 104 of outer cannula 100. Thus, while FIG. 2 illustrates trocar 120 as a solid shaft, variations as would occur to a person of ordinary skill in the art for the connection between the distal end 124 and the proximal end 122 of trocar 120 are contemplated as within the scope of the invention.

Figure 12:
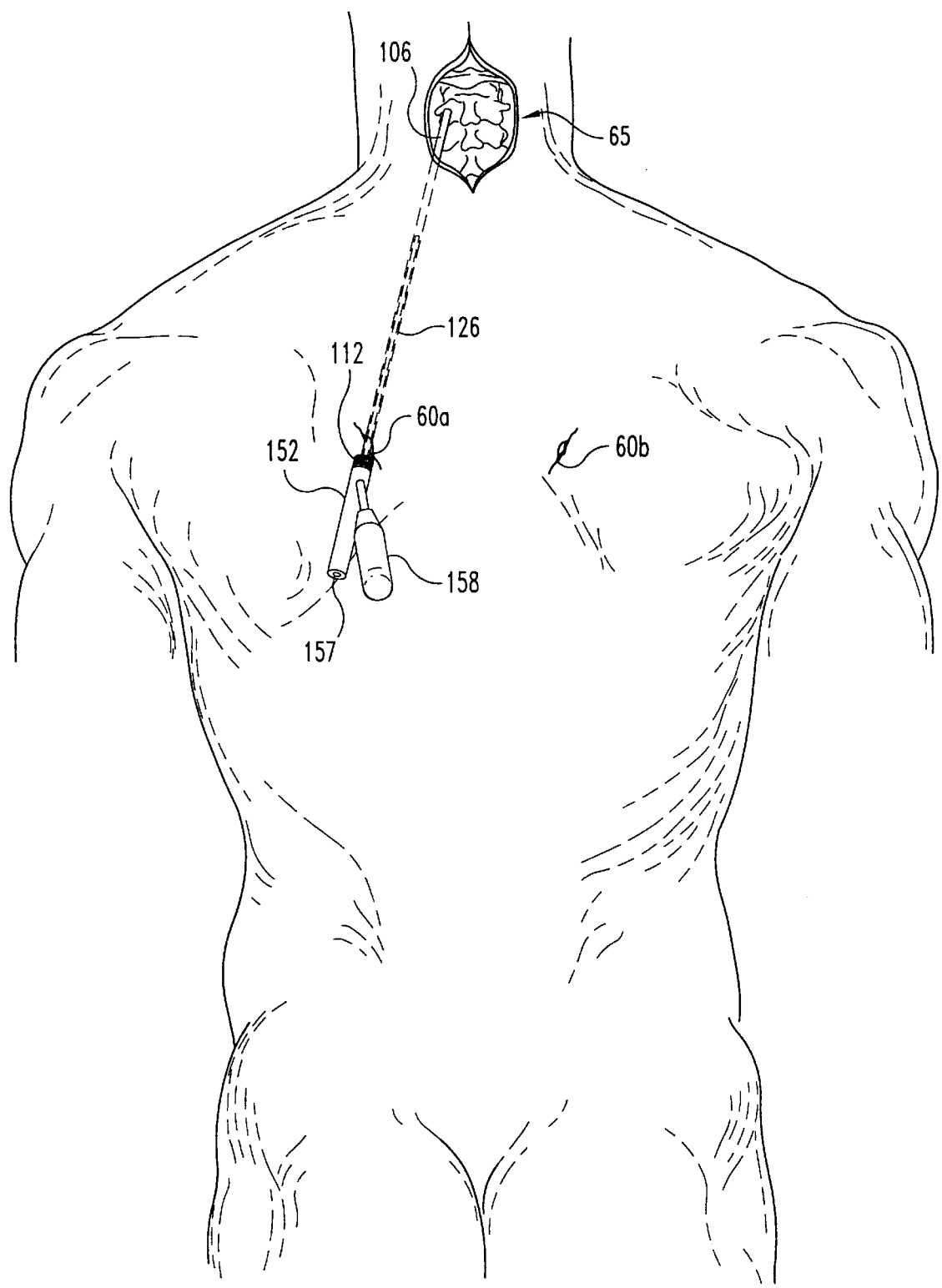
FIG. 12 is a top view of the use of the screw delivery system of the present invention on a patient lying prone with the surgical site in the cervical vertebra region.

The trocar 120 has a length such that when inserted through the bore 101a of outer cannula 100, the bullet-shaped head 130 will extend past the tip 110 of outer cannula 100. When the trocar 120 is inserted as far as possible through the bore 101a of outer cannula 100, the front face 132a of the annular flange 132 will contact the rear face 112b of stop 112 of outer cannula 100 (see FIG. 11). At or near this point the bullet-shaped head 130 will extend past the tip 110 of outer cannula 100 thus permitting the trocar 120 and outer cannula 100 to be percutaneously inserted through an incision 50 distal from the surgical site 55. Thus, despite the fact that the desired entry angle for transarticular screw fixation is very small, the large midline incision of current techniques is unnecessary. Only a small midline incision directly over the surgical site is necessary, as the passageway provided by bore 101a of outer cannula 100 of the screw delivery system permits the introduction of all the tools, implants, and interventional devices necessary to stabilize the spine using transarticular screw fixation. It should be understood that while the illustration of FIG. 11 demonstrates the applicability of the soft tissue penetrator combination of trocar 120 with outer cannula 100 in the lumbar vertebra of the spine, the screw delivery system of the present invention is equally useful for avoiding the necessity of a large midline incision when a surgical site is, for example, in a cervical vertebra as is the case in a transarticular screw fixation across the atlanto-axial joint (see FIG. 12).

Figure 3:
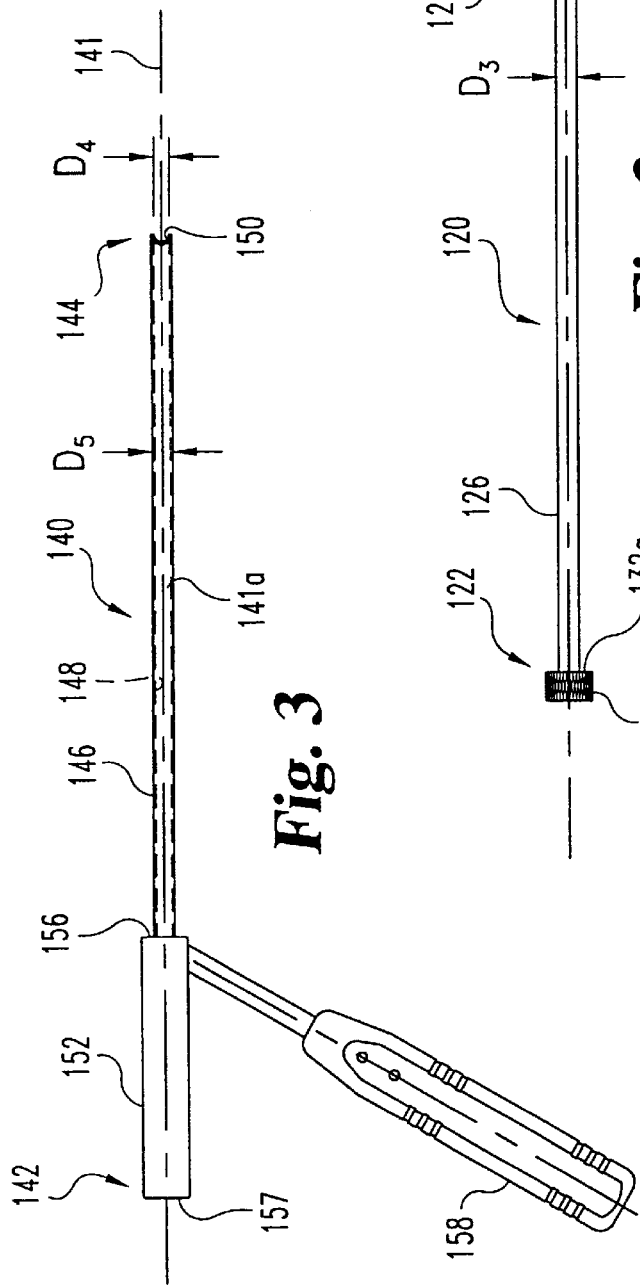
FIG. 3 is a side view of a guide for insertion into the outer cannula of FIG. 1 for more accurately directing the bone drill bits and taps of FIGS. 4–6.

The devices used through the bore 101a of outer cannula 100 in various embodiments of the present invention are illustrated in FIGS. 3–9 and are discussed in more detail below. After the details of the individual components of various embodiments of the present invention are outlined, the method of their use will be discussed in further detail. With reference to FIG. 3, there is illustrated one embodiment of a device for more accurately aiming various embodiments of bone drill bits and bone taps to the appropriate lengths. The guide 140 generally extends along a longitudinal axis 141 (with the exception of the handle 158). The guide 140 has a bore 141a defined by an interior surface 148 extending between the proximal end 142 and the distal end 144. The guide 140 has an exterior surface 146 defined between the proximal end 142 and the distal end 144 which terminates in a tip 150. The proximal end 142 of the guide 140 has an annular flange or stop 152 with a front face 156 and a rear face 157. The exterior surface 146 has an outer diameter D5 and the interior surface 148 has an inner diameter D4.

The guide 140 has a handle 158 which is connected at an angle to the stop 152. It should be understood, however, that the handle 158 may be located/connected at a variety of locations. The handle 158 is at an angle transverse to the longitudinal axis 141. The angle of the handle is relevant to many of the applications with small entry angles as it should not be perpendicular to the longitudinal axis 141. It should also be understood that the angle that the handle 158 makes with respect to the longitudinal axis 141 is preferably less than 60 degrees. The outer diameter D5 is greater than the inner diameter D4, but is less than the inner diameter D1 of the outer cannula 100. Thus, the exterior surface 146 may be inserted through the bore 101a of outer cannula 100 until the front face 156 of guide 140 contacts the rear face 112b of stop 112 of outer cannula 100. As discussed further below, when the front face 156 is in contact with the rear face 112b of a stop 112 of outer cannula 100, various other instruments are inserted through the bore 141a as well as the bore 101a such as the bone drill bits 160, 180, and tap 200 discussed below.

With reference to FIG. 4A, there is illustrated a side view of a standard bone drill bit 160 extending along an axis 161 between a proximal end 162 and a drilling end 164. The proximal end 162 has a surface adapted for the application of force to rotate the bone drill bit 160. In one embodiment, as illustrated in FIG. 4A, the standard bone drill bit 160 has a half solid cylinder 163a and a flattened portion 163b at the proximal end 162 to permit rotation of the standard bone drill bit 160. With reference to FIGS. 4A and 4B, the drilling end 164 has a plurality of flutes 165 and a standard drill tip 170. Standard bone drill bit 160 has an exterior surface 166 extending between the front face 172a of annular flange or stop 172 and the beginning of the flutes 165 making up the drilling end 164 of standard bone drill 160. The exterior surface 166 of standard bone drill 160 has an outer diameter D6. Additionally, the portion of exterior surface 166 near annular flange or stop 172 preferably has a plurality of length markings 167.

With reference to FIGS. 5A and 5B, there is illustrated the preferred embodiment of a bone drill bit 180 for use in the screw delivery system and method of the present invention.

It should be understood that due to the small entry angle between the bone drill bit and the bone in the spine/vertebra of the surgical site, that a standard bone drill bit 160 has a blunt end that is difficult to get started. The tip 170 of the bone drill bit 160 has a tendency to walk along the surface, making accurate placement difficult. Thus, the more preferred embodiment is bone drill bit 180 which extends along an axis 181 between a proximal end 182 and drilling end 184. Similar to the standard bone drill bit, the preferred bone drill 180 has a half solid cylinder 183a and a flattened portion 183b at proximal end 182 for use in rotating the bone drill bit 180. The drilling end 184 of bone drill bit 180 has a plurality of flutes 185. Bone drill bit 180 has an exterior surface 186 extending between the front face 192a of annular flange or stop 192 and the beginning of the plurality of flutes 185 on the drilling end 184. Bone drill bit 180 has a sharper angled drill tip 190 at the end of drilling end 184 which permits ease of insertion when beginning to drill even at the small entry angles preferably less than 45° (not perpendicular to bone) for the methods of use of the screw delivery system discussed further below. The exterior surface 186 of bone drill bit 180 has an outer diameter D7. Both outer diameter D7 and outer diameter D6 are less than the inner diameter D4 of guide 140. In a preferred embodiment, the guide 140 has an inner diameter D4 which is only slightly larger than the outer diameter D6 or outer diameter D7 of bone drills 160, 180, respectively. This permits more accurate placement of the drill tips 170, 190 and minimizes deviations from side to side of the axis 161, 181, respectively when drilling.

With reference to FIG. 6 there is illustrated a side view of a bone tap 200 for use with a screw delivery system of the present invention. Bone tap 200 extends along axis 201 between proximal end 202 and tapping end 204. Similar to the bone drill bits 160, 180, the proximal end 202 of tap 200 has a solid half cylinder 203a and a flattened portion 203b to permit rotation of the bone tap 200. As is understood by those of ordinary skill in the art, the tapping end 204 of bone tap 200 has threading 205 thereon and a tip 210 for creating threading in the opening or bore in the bone created by a bone drill bit 160, 180. Bone tap 200 has an exterior surface 206 extending between the front surface 212a of annular flange or stop 212 and the beginning of the threading 205 at the tapping end 204. The exterior surface 206 has an outer diameter D8 which is less than the inner diameter D4 of the guide 140 to permit the bone tap 200 to be inserted through the bore 141a of guide 140. As with the bone drill bits 160, 180, the exterior surface 206 of bone tap 200 preferably has a plurality of length markings 207 on the portion of exterior surface 206 adjacent the annular flange or stop 212.

With reference to FIGS. 7 and 8 there are illustrated side views for the cutter (FIG. 7) and the adjustable length stop (FIG. 8). In particular with reference to FIG. 7, cutter 220 has handles 222, 223 which are pivotally connected around hinge 224. The cutting end 226 of cutter 220 is made up of a first cutting element 230 and a second cutting element 235. The first cutting element 230 has a first sharp edge 231 adjacent a circular depression 232 which has its own cutting edge 233. Similarly, second cutting element 235 has a second sharp edge 236 adjacent another circular depression 237 having its own cutting edge 238. It should be understood that cutter 220 is intended for use on the adjustable length stop 240 as illustrated in FIG. 8.

The adjustable length stop 240 has integrally connected individual cylindrical elements 242 with a length L and an inner diameter D9 and an outer diameter D10. The individual cylindrical elements 242 of adjustable length stop 240 extend along a longitudinal axis 241. The individual cylindrical elements 242 of the adjustable length stop 240 define a bore 248 extending along the axis 241. In one embodiment, the length L of the individual cylindrical elements 242 corresponds to the distance between the length markings such as length markings 207 on bone tap 200, length markings 187 on bone drill bit 180, and/or length markings 167 on bone drill bit 160. It is contemplated as within the scope of the invention, however, that the length of the individual cylindrical elements may be different than that of the markings on the respective bone drill bits and taps, and that the length of each individual cylindrical element may vary on a single adjustable length stop 240. It should be understood that the inner diameter D9 of bore 248 of the adjustable length stop 240 should be greater than diameters D8, D7, D6, but is less than D5 which in turn is less than D1 which is less than D2. It should also be understood that the outer diameter D10 should be greater than either the outer diameter D5 of the guide 140 or at least of a sufficient diameter so that the adjustable length stop 240 will act as a contact mechanism to prevent further insertion of the bone drills or bone taps upon contacting the rear face 157 of annular flange or stop 152 of the guide 140. Similarly, in those embodiments of the device where a guide 140 is not utilized, but instead only the outer cannula 100 is, the outer diameter D10 should be such that the adjustable length stop 240 will contact the rear surface 112b of annular flange or stop 102 of outercannula 100.

With reference to FIG. 9, there is illustrated a side view of an implant driver in the form of a screwdriver 260 for use with the screw delivery system of the present invention. Screwdriver 260 extends generally along axis 261 between a proximal end 262 and distal end 264. Screwdriver 260 comprises a handle 278 which has a front face 276. Front face 276 of handle 278 could act as a stop, but in general the length of the screwdriver 260 is made deliberately long so that whatever screw used may be screwed in as deep as may be deemed necessary. Screwdriver 260 has an exterior surface 266 with an outer diameter D11 extending between the front face 276 of handle 278 and the tip 270 at distal end 264. The tip 270 of screw driver 260 is configured so as to fit within the screw head of the screw used for transarticular screw fixation and other surgeries as contemplated within the scope of the invention. In general the tip 270 of screwdriver 260 will define a polygonal shape which will mate with a polygonal socket of the same shape in the screw head of the screw used. For ease of reference, the relationship among diameters of various components is summarized below:

$D_3 < D_1$
$D_8$
$D_7 < D_4 < D_5 < D_1 < D_2$
$D_6$
$D_8$
$D_7 < D_9 < D_{10}$
$D_6$
$D_{11} < D_2$

Having now described the individual elements of the screw delivery system, the general method of use will now be described. The screw delivery system of the present invention is particularly useful for three primary surgical indications. The first indication is use in repair of a odontoid fracture. The second indication is transarticular screw fixation across the first and second cervical vertebrae. The third indication is transarticular screw fixation across the lumbar facet joint. All of these indications will be discussed with more specificity below. The general procedure, however, essentially entails seizing the joint between the vertebrae and immobilizing it until either the fracture heals (as in the first indication) or until fusion occurs (as in the second or third indications). It should be understood that the first indication is an anterior procedure while the second and third indications are posterior procedures.

In the generalized method of use, the soft tissue penetrator or introducer in the form of the outer cannula 100 with the trocar 120 having a bullet-shaped head 130 is introduced through an incision 50 in the skin on the back and directed toward the surgical site (in FIG. 11 the surgical site is across lumbar vertebra) viewed through incision 55. The tip 110 of the outer cannula 100 is then seated on the portion of the bone or vertebra at the appropriate angle for the introduction of the screw for fixation. The bullet-shaped head 130, and indeed the entire trocar 120, are then removed from the outer cannula 100. Then, the distal end 144 of the drill guide 140 is inserted through the near end 102 of outer cannula 100 until the front face 156 of stop 152 of guide 140 contacts the rear face 112b of annular flange or stop 112 of outer cannula 100. Next, the drilling end 184 of bone drill bit 180 is inserted through the bore 141a of guide 140 past the distal end 144 and then on into the bore 101a of outer cannula 100. It should be understood that the surgeon could use a high speed burr to mark the point of insertion of the screw, but this generally weakens the fixation of the screw's strength because of the loss of cortical bone on the outside surface of the vertebra. Instead, it is preferable, as mentioned above, to use the improved drill bit 180 of the present invention which has a sharper angled drill tip 190 which permits easier insertion during the beginning of the drilling process despite the very small entry angle commonly encountered in transarticular screw fixation across vertebral joints.

As previously mentioned, the bone drill bit 180 has a plurality of length markings 187 adjacent the annular flange or stop 192. The length markings 187 allow the surgeon to know the distance the drill has been drilled into the bone at a glance by examining the length markings 187 of the bone drill bit 180. The screws (not shown) to be used are of a fixed length which can be measured. Based on this fixed length, an adjustable length stop 240 is inserted onto either the bone drill bit 180 or tap 200 as appropriate. The exterior surface 186, 206 of the bone drill bit 180 or tap 200, respectively, is inserted through the bore 248 of the adjustable length stop 240. In general, both the bone tap 200 and the bone drill bit 180 will be marked with 30 mil projections in 5 mm increments. Similarly, the length L of the individual cylindrical elements 142 of the adjustable length stop 140 will generally be equal to these 5 mm increments of the length markings 207 and 187. The adjustable length stop 240 is simple and does not change the lengths of the guide 140 permitting the use of one standard guide 140 and of standard length bone drill bits 180 and bone taps 200. The variable is the adjustable length stop 240, which is generally constructed of plastic, allowing the use of a cutter 220 to trim the total length of the adjustable length stop 240, thus permitting the desired length of insertion of the bone drill bit 180 and bone tap 200. The cutter 220 may either cut off individual cylindrical elements 242 to alter the length L of adjustable length stop 240 or may even be used to cut through an individual cylindrical element 242. It should be understood that it is generally preferable if the cutter 220 is used to cut to total length the adjustable length stop 240 by trimming through the weakened portion between the individual cylindrical elements which is intended to break off.

After trimming the adjustable length stop 240 to the desired total length, the bone drill bit 180 is inserted through the bore 141a of the guide 140 and the bore 101a of the concentric outer cannula 100 and the drill is rotated and an opening in the bone is created by advancing the bone drill bit 180 along axis 181 until the adjustable length stop 240 contacts the rear face 157 of stop 152 of the guide 140 which prevents further advancement of the bone drill bit 180 into the bone. The bone drill bit 180 is then removed from both the guide 140 and outer cannula 100. Next, the bone tap 200 is introduced through the bores 141a and 101a. The bone tap 200 will have an adjustable length stop 240 of the same total length as that used on the guide 140. The opening in the bone created by the bone drill bit 180 is then threaded by rotating and advancing bone tap 200 until the adjustable length stop 240 on bone tap 200 contacts the rear face 157 of stop 152 on guide 140.

After the opening in the bone portion has been drilled and tapped, the entire inner sleeve in the form of the bone tap 200 and guide 140 is removed from the outer cannula 100. Next, a screw and implant driver are introduced through the near end 102 of outer cannula 100. The implant driver will generally be a standard screwdriver 260 having a tip 270 with a polygonal head which will mate with a same shaped polygonal socket in the head of the screw (not shown) to be driven into the bone. The screw and screwdriver 260 are inserted through the bore 101a of outer cannula 100 until they have reached the opening located beyond the tip 110 of the far end 104 of outer cannula 100. The location of this opening will vary depending on the indication as described further below.

As mentioned above, the first indication of particular use for the screw delivery system and method of the present invention is for use with an odontoid fracture. An odontoid fracture is a special type of C2 (second cervical vertebra) or axis vertebra. As mentioned in the background section, the odontoid is a prominent process, tooth-like in form, projecting perpendicularly upward from the axis vertebra toward the atlas vertebra. In the past, odontoid fractures were treated by the use of halo. The alternative treatment mechanism is to insert a screw across the fracture site. This will be an anterior procedure through the neck, so that operating through the bore 101a of the outer cannula 100 aids in protecting important structures in the neck as well as providing a minimally invasive procedure generally.

Odontoid screw fixation is a technically demanding procedure that requires thorough preoperative planning and adequate surgical training. The entry point is critical at the anterior margin of the inferior endplate. If started more cephalad, the angle of inclination for fracture fixation cannot be achieved and anterior gapping of the fracture is a common result. Also, poor proximal fragment purchase with subsequent screw cut-out may occur. It is important to engage the far cortex of the odontoid tip to ensure adequate purchase and it is mandatory to lag the fracture fragments either through screw design or by creating a gliding hole through the body fragment. AP and lateral fluoroscopy is essential for constant monitoring during all stages of this procedure.

Odontoid screw fixation using the screw delivery system of the present invention is a combination of percutaneous and open technique to make a minimally invasive approach. The surgeon actually views the entry site of the screw and through a separate incision places the screw delivery system while viewing where the far end 104 of the outer cannula 100 is going to dock. The technique is generally done using biplanar fluoroscopy, which allows viewing of the fracture on TV screens as you place the drill, tap and screw, respectively, across it during the procedure. The entirety of drilling, tapping, and screw insertion is done through the working sleeve in the form of the outer cannula 100 and drill guide 140, as previously discussed.

Figure 10:
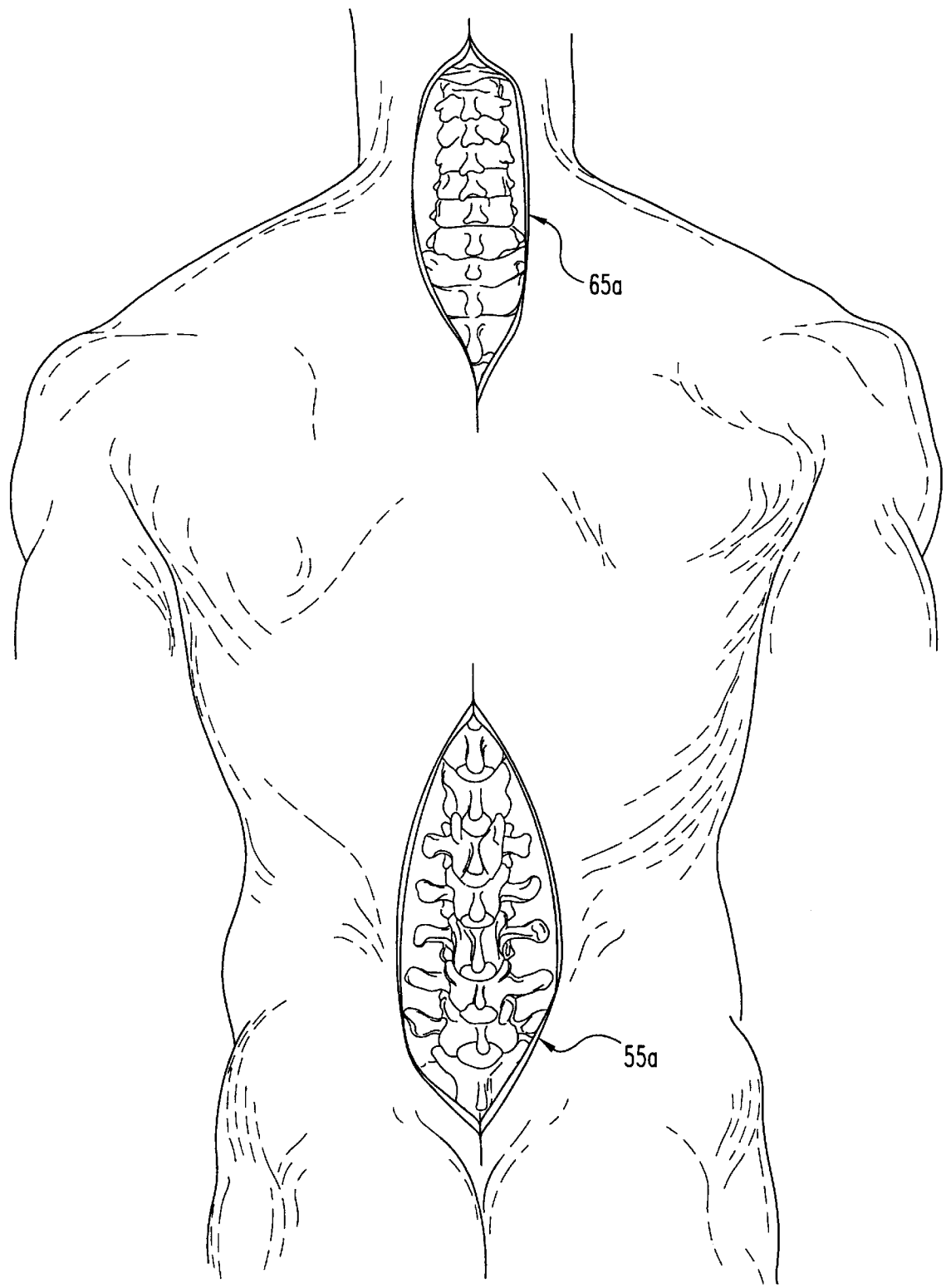
FIG. 10 is a top view of the back of a patient lying prone illustrating the size of the prior art incision made in the cervical and lumbar regions for transarticular screw fixation.

The specifics of the screw entry angle and placement for the second indication, transarticular screw fixation of the C1 and C2 (atlas and axis) vertebra are described in the articles previously incorporated by reference and will not be discussed in any detail here. Suffice it to say that the desired result is the fusion of C1 and C2 together using a posterior approach wherein the screw goes across the C1/C2 joint in the back. Using the standard technique generally requires a very long incision in order to get the appropriate trajectory. The incision would have to be made all the way into the thoracic area of the spine in order to get the correct entry angle since it is a very steep shot for the drill, tap, and screw, respectively. Indeed, the articles describing the standard technique recommend making an incision from C1 all the way down to C7 (see incision 65a of FIG. 10). In contrast, the use of the screw delivery system and method of the present invention requires only a small midline incision 65 (see FIG. 12) at the C1/C2 region and two percutaneous incisions 60a and 60b (see FIG. 12) around the upper thoracic area through which the screw delivery system of the present invention is introduced and directed toward the surgical site at the joint between C1 and C2. This surgical site is viewed directly through the small midline incision 65 made.

The third indication mentioned above as deriving particular benefit through use of the screw delivery system of the present invention is placing a screw across a lumbar facet joint to fuse the joint between two lumbar vertebra. This may be done rather than putting pedicle screws in and then attaching those anchors (the pedicle screws) to a rod, plate or other longitudinal element spanning the intervertebral disc or the space left behind after it is excised. Instead, in this procedure, the surgeon simply places two screws in the shape of an X (when viewed from above a prone patient) across the lumbar facet joint. This is usually done in combination with an anterior interbody fusion which has more recently undergone an upsurge in popularity with the use of devices known as cages. The benefits of simply putting screws across the lumbar facet joint as to the more complex apparatus involving insertion of pedicle screws and attaching longitudinal elements to the anchors is that putting screws across the lumbar facet joint results in a very, very low profile implant.

Again, this third indication is a minimally invasive procedure which is a combination of percutaneous and open techniques. As with the cervical fusion described in the second indication, a small midline incision 55 (see FIG. 11) is made over the two vertebra to be fused which goes right down to the facet joint. Each screw goes across the lamina from the posterior spinous process, being driven across the facet joint which is out laterally and downstream. The entry point for the drill bit (and the tap and screw) is again out and aside, up in the flank. The joint between the lumbar vertebrae is fairly deep and the exit point of the drill bit and the screw is intended to be fixed deep into the joint. The screw's entry point is the posterior spinous process on the contralateral side. The screw travels between the anterior and posterior cortices of the laminae to enter the inferior articular process. The screw then crosses the facet joint—entering the superior articular process and then exiting at the base of the transverse process and pars interarticularis.

The screw delivery system of the present invention is beneficial, both in the three indications described above, as well as in other procedures known to those of ordinary skill in the art. The screw delivery system of the present invention permits the making of one or more small percutaneous portals through which the implant and interventional devices are introduced. After making an incision at midline or otherwise permitting viewing of the surgical site, the docking part of the multi-sleeve device of the screw delivery system of the present invention is introduced and directly abuts the surgical site as desired. Then a surgeon may drill, tap, and insert the screw through the percutaneous portal provided by the screw delivery system of the present invention.

While the invention has been illustrated and described in detail in the drawings and foregoing description, the same is to be considered illustrative and not restrictive in character, it being understood that only the preferred embodiments have been shown and described and that all changes and modifications that come within the spirit of the invention are desired to be protected.

What is claimed:

1. A screw delivery system kit, comprising:

an outer cannula having a first exterior surface and a first interior surface defining a bore, the first interior surface having a first inner diameter and the first exterior surface having a first outer diameter, the surfaces extending along a first length on a first axis between a first proximal end having a first stop and a first distal end;

a trocar having a second exterior surface with a second outer diameter, the second exterior surface extending along a second length on a second axis between a second proximal end having a second stop and a second distal end defining a blunt tip;

a guide having a handle and a tube, the tube having a third exterior surface and a third interior surface defining a passageway, the third interior surface having a third inner diameter and the third exterior surface having a third outer diameter, the third interior surface extending between a third proximal end and a third distal end, the third exterior surface extending along a third length on a third axis between a third stop at the third proximal end and the third distal end, the handle being connected to the tube at an angle to the third axis;

a bone drill bit having a fourth exterior surface with a fourth outer diameter extending along a fourth length on a fourth axis between a fourth stop located near a fourth proximal end and a plurality of drilling flutes defined on a fourth distal end;

a bone tap having a fifth exterior surface with a fifth outer diameter extending between a fifth stop located near a fifth proximal end and a fifth distal end having threading thereon for tapping an opening in bone created by said bone drill bit;

an adjustable length stop having a length, the adjustable length stop being a series of interconnected cylindrical elements;

a cutter for adjusting the length of said adjustable length stop; and, an implant driver for inserting a screw.

2. The kit of claim 1, further comprising at least one interbody fusion implant.

3. The kit of claim 1, further including a screw adapted for screwing at least one screw across a facet joint of the vertebrae.

4. The kit of claim 3, further comprising at least one interbody fusion implant.

5. The kit of claim 1, wherein the fifth exterior surface has a plurality of length markings adjacent the fifth stop, the length markings being located on the fifth exterior surface between the fifth stop and the fifth distal end of said bone tap.

6. The kit of claim 1, wherein the fourth exterior surface has a plurality of length markings adjacent the fourth stop, the length markings being located on said fourth exterior surface between the fourth stop and the fourth distal end.

7. The kit of claim 1, wherein said adjustable length stop has an outer surface and an inner surface defining a bore with a bore diameter, the bore diameter of said adjustable length stop being greater than the fourth outer diameter.

8. The kit of claim 7, further comprising at least one interbody fusion implant.

9. A method of inserting a screw into vertebral bone in the lumbar region or the spine, comprising:

making an incision for percutaneous access to a surgical site;

inserting an outer cannula having a bore defined between a proximal end and a distal end and a trocar through the bore into the incision;

advancing the outer cannula and trocar toward the surgical site until the distal end of the outer cannula is positioned adjacent the surgical site;

removing the trocar from the outer cannula;

forming an opening through a first lumbar vertebra and into a second lumbar vertebra;

delivering a screw through the bore of the outer cannula to the surgical site; and screwing the screw into the opening through the first lumbar vertebra and into the second lumbar vertebra.

10. The method of claim 9, further comprising tapping the opening before screwing the screw into the opening.

11. The method of claim 9, further comprising positioning at least one interbody fusion implant between the first and second lumbar vertebrae.

12. The method of claim 9, wherein the screwing comprises engaging the screw across a joint of the first and second lumbar vertebrae.

13. The method of claim 12, wherein the joint is a lumbar facet joint.

14. The method of claim 13, wherein the screwing comprises transarticular screw fixation across the lumbar facet joint.

15. The method of claim 13, wherein the engaging of the screw across the lumbar facet joint facilitates fusion between the first and second lumbar vertebrae.

16. The method of claim 13, wherein two of the screws are engaged across the lumbar facet joint.

17. The method of claim 16, wherein the two screws are engaged across the lumbar facet joint in a cross-over configuration.

18. The method of claim 13, wherein the opening through the first lumbar vertebra extends from the posterior spinous process and through the lamina to the lumbar facet joint.

19. The method of claim 18, wherein the opening through the first lumbar vertebra extends from the contralateral side of the posterior spinous process.

20. The method of claim 18, wherein the opening through the first lumbar vertebra extends across the anterior and posterior cortices of the lamina to the inferior articular process.

21. The method of claim 20, wherein the opening into the second lumbar vertebra extends from superior articular process.

22. The method of claim 21, wherein the opening extends through the second lumbar vertebra from the superior articular process to the base of the transverse process and pars interarticularis.

23. The method of claim 13, wherein the screwing comprises transarticular screw fixation cross the lumbar facet joint.

24. The method of claim 9, wherein the access incision is remote from the surgical site; and
   wherein the method further comprises making a second incision over the surgical site for viewing the surgical site.

25. A method of facilitating interbody fusion between a first vertebra and a second vertebra, comprising:
   making an incision for percutaneous access to a surgical site;
   inserting an outer cannula having a bore defined between a proximal end and a distal end and a trocar through the bore into the incision;
   advancing the outer cannula and trocar toward the surgical site until the distal end of the outer cannula is positioned adjacent the surgical site;
   removing the trocar from the outer cannula;
   forming an opening through the first vertebra and into the second vertebra;
   delivering a screw through the bore of the outer cannula to the surgical site;
   screwing the screw into the opening through the first vertebra and into the second vertebra; and
   positioning at least one interbody fusion implant between the first and second vertebrae.

26. The method of claim 25, further comprising tapping the opening before screwing the screw into the opening.

27. The method of claim 25, wherein the screwing comprises engaging the screw across a joint of the first and second vertebrae.

28. The method of claim 27, wherein the first and second vertebrae are lumbar vertebrae.

29. The method of claim 27, wherein the joint is a lumbar facet joint.

30. The method of claim 27, wherein the screwing comprises transarticular screw fixation across the joint.

31. The method of claim 27, wherein two of the screws are engaged across the joint.

32. The method of claim 25, wherein the access incision is remote from the surgical site; and
   wherein the method further comprises making a second incision over the surgical site for viewing the surgical site.

\* \* \* \* \*